United States Patent
Coy et al.

(10) Patent No.: US 7,312,304 B2
(45) Date of Patent: Dec. 25, 2007

(54) SOMATOSTATIN AGONISTS

(75) Inventors: David H. Coy, New Orleans, LA (US); Walajapet G. Rajeswaran, Kalamazoo, MI (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 10/474,248

(22) PCT Filed: Apr. 8, 2002

(86) PCT No.: PCT/US03/10882

§ 371 (c)(1),
(2), (4) Date: Apr. 26, 2004

(87) PCT Pub. No.: WO02/081499

PCT Pub. Date: Oct. 17, 2002

(65) Prior Publication Data

US 2004/0171530 A1    Sep. 2, 2004

Related U.S. Application Data

(60) Provisional application No. 60/282,526, filed on Apr. 9, 2001.

(51) Int. Cl.
*A61K 38/22* (2006.01)
*A61K 38/04* (2006.01)
*A61K 38/00* (2006.01)

(52) U.S. Cl. ............... 530/313; 530/317; 530/328; 514/11; 514/16; 514/9

(58) Field of Classification Search .............. 514/2, 514/9, 11, 16; 530/300, 311, 313, 317, 328; 424/278.1
See application file for complete search history.

(56) References Cited

U.S. PATENT DOCUMENTS

| | | | |
|---|---|---|---|
| 5,462,926 A * | 10/1995 | Coy et al. | 514/16 |
| 5,506,339 A * | 4/1996 | Coy et al. | 530/311 |
| 5,633,263 A | 5/1997 | Coy et al. | |
| 6,004,928 A | 12/1999 | Cawthorne et al. | |
| 6,025,372 A | 2/2000 | Yang et al. | |
| 6,051,206 A * | 4/2000 | Dean et al. | 424/1.69 |
| 6,262,229 B1 * | 7/2001 | Coy et al. | 530/311 |
| 6,703,481 B1 * | 3/2004 | Coy et al. | 530/311 |
| 7,060,679 B2 * | 6/2006 | Hornik et al. | 514/9 |
| 2004/0181032 A1 * | 9/2004 | Coy et al. | 530/317 |

FOREIGN PATENT DOCUMENTS

WO          98/08529         3/1998

OTHER PUBLICATIONS

Wikipedia (2007, updated) "IC50", http://en.wikipedia.org/wiki?IC50, p. 1.*
Rajeswaran, W. G. et al., "N-Methyl Scan of Somatostatin Octapeptide Agonists Produces Interesting Effects on Receptor Subtype Specificity," J. Med. Chem., 2001, 44:1416-1421.
Bauer, W., et al., "SMS 201-995: A very potent and selective octapeptide analogue of somatostatin with prolonged action," Life Sciences, 1982, 31(11):1133-1140.
Coy, D., et al., "Solid phase reduction alkylation techniques in analogue peptide bond and side chain modification," Tetrahedron, 1988, 44(3):835-841.
Mattern, R-H., et al., "Synthesis, biological activities and conformational studies of somatostatin analogs," Tetrahedron, 2000, 56(50):9819-9831.
Miller, S. C., et al., "Site-selective N-methylation of peptides on solid support," J. Amer. Chem. Soc., 1997, 119:2301-2302.
Sasaki, Y., et al., "Solid-phase synthesis and biological properties of pseCH2NH pseudopeptide analogues of a highly potent somatostatin octapeptide," J. Medicinal Chem., 1987, 30(7):1162-1166.

* cited by examiner

*Primary Examiner*—Kathleen Kerr Bragdon
*Assistant Examiner*—Samuel Wei Liu
(74) *Attorney, Agent, or Firm*—Yankwich & Associates; Alan F. Feeney; Pamela C. Ball

(57) ABSTRACT

Claimed are a series of somatostatin agonists and uses thereof, according to formula (I), $$A^1\text{-cyclo}[Cys\text{-}A^2\text{-D-Trp-}A^3\text{-}A^4\text{-Cys}]\text{-}A^5\text{-}Y^1, \quad (I)$$

wherein $A^1$, $A^2$, $A^3$, $A^4$, $A^5$ and $Y^1$ are as defined in specification provided that the amine nitrogen of at least one peptide bond is substituted with a methyl group or pharmaceutically acceptable salts thereof.

20 Claims, No Drawings

SOMATOSTATIN AGONISTS

CROSS REFERENCE TO RELATED APPLICATIONS

This application is a United States national filing under 35 U.S.C. §371 of international (PCT) application No. PCT/US02/10882, filed Apr. 8, 2002, designating the U.S., and claiming priority to U.S. provisional application No. 60/282,526, filed Apr. 9, 2001.

BACKGROUND OF THE INVENTION

Somatostatin (SRIF), a tetradecapeptide discovered by Brazeau et al., has been shown to have potent inhibitory effects on various secretory processes in tissues such as pituitary, pancreas and gastrointestinal tract. SRIF also acts as a neuromodulator in the central nervous system. These biological effects of SRIF, all inhibitory in nature, are elicited through a series of G protein coupled receptors, of which five different subtypes have been characterized and are referred to as somatostatin type-1 receptor to somatostatin type-5 receptor (SSTR-1 to SSTR-5). These five subtypes have similar affinities for the endogenous SRIF ligands but have differing distribution in various tissues. SRIF binds to the five distinct receptor (SSTR) subtypes with relatively high and equal affinity for each subtype. SRIF produces a variety of effects, including modulation of hormone release, e.g., growth hormone, glucagon, insulin, amylin, and neurotransmitter release. Some of these effects have been associated with its binding to a specific SRIF receptor. For example, the inhibition of growth hormone has been attributed to the somatostatin type-2 receptor ("SSTR-2") (Raynor, et al., Molecular Pharmacol. 43:838 (1993); Lloyd, et al., Am. J. Physiol. 268:G102 (1995)), while the inhibition of insulin has been attributed to the somatostatin type-5 receptor ("SSTR-5") (Coy, et al. 197:366-371 (1993)). Activation of types 2 and 5 have been associated with growth hormone (GH) suppression and more particularly GH secreting adenomas (acromegaly) and thyroid-stimulating hormone (TSH) secreting adenomas. Activation of type 2 but not type 5 has been associated with treating prolactin secreting adenomas.

As is well known to those skilled in the art, SRIF and analogs thereof are useful in the treatment of a great variety of diseases and/or conditions. An exemplary but by no means exhaustive list of such diseases and/or conditions would include: Cushing's Syndrome (see Clark, R. V. et al, Clin. Res. 38, p. 943A, 1990); gonadotropinoma (see Ambrosi B., et al., Acta Endocr. (Copenh.) 122, 569-576, 1990); hyperparathyroidism (see Miller, D., et al., Canad. Med. Ass. J., Vol. 145, pp. 227-228, 1991); Paget's disease (see, Palmieri, G. M. A., et al., J. of Bone and Mineral Research, 7, (Suppl. 1), p. S240 (Abs. 591), 1992); VIPoma (see Koberstein, B., et al., Z. Gastroenterology, 28, 295-301, 1990 and Christensen, C., Acta Chir. Scand. 155, 541-543, 1989); nesidioblastosis and hyperinsulinism (see Laron, Z., Israel J. Med. Sci., 26 No. 1, 1-2, 1990, Wilson, D. C., Irish J. Med. Sci., 158, No. 1, 31-32, 1989 and Micic, D., et al., Digestion, 16, Suppl. 1.70. Abs. 193, 1990); gastrinoma (see Bauer, F. E., et al., Europ. J. Pharmacol., 183, 55 1990); Zollinger-Ellison Syndrome (see Mozell, E., et al., Surg. Gynec. Obstet., 170, 476-484, 1990); hypersecretory diarrhea related to acquired immunodeficiency syndrome (AIDS) and other conditions (due to AIDS, see Cello, J. P., et al., Gastroenterology, 98, No. 5, Part 2, Suppl., A163 1990; due to elevated gastrin-releasing peptide, see Alhindawi, R., et al., Can. J. Surg., 33, 139-142, 1990; secondary to intestinal graft vs. host disease, see Bianco J. A., et al., Transplantation, 49, 1194-1195, 1990; diarrhea associated with chemotherapy, see Petrelli, N., et al., Proc. Amer. Soc. Clin. Oncol., Vol. 10, P 138, Abstr. No. 417 1991); irritable bowel syndrome (see O'Donnell, L. J. D., et al., Aliment. Pharmacol. Therap., Vol. 4., 177-181, 1990); pancreatitis (see Tulassay, Z., et al., Gastroenterology, 98, No. 5, Part 2, Suppl., A238, 1990); Crohn's Disease (see Fedorak, R. N., et al., Can. J. Gastroenterology, 3, No. 2, 53-57, 1989); systemic sclerosis (see Soudah, H., et al., Gastroenterology, 98, No. 5, Part 2, Suppl., A129, 1990); thyroid cancer (see Modigliani, E., et al., Ann., Endocr. (Paris), 50, 483-488, 1989); psoriasis (see Camisa, C., et al., Cleveland Clinic J. Med., 57, No. 1, 71-76, 1990); hypotension (see Hoeldtke, R. D., et al., Arch. Phys. Med. Rehabil., 69, 895-898, 1988 and Kooner, J. S., et al., Brit. J. Clin. Pharmacol., 28 735P-736P, 1989); panic attacks (see Abelson, J. L., et al., Clin. Psychopharmacol., 10, 128-132, 1990); scleroderma (see Soudah, H., et al., Clin. Res., Vol. 39, p. 303A, 1991); small bowel obstruction (see Nott, D. M., et al., Brit. J. Surg., Vol. 77, p. A691, 1990); gastroesophageal reflux (see Branch, M. S., et al., Gastroenterology, Vol. 100, No. 5, Part 2 Suppl., p. A425, 1991); duodenogastric reflux (see Hasler, W., et al., Gastroenterology, Vol. 100, No. 5, Part 2, Suppl., p. A448, 1991); Graves' Disease (see Chang, T. C., et al., Brit. Med. J., 304, p. 158, 1992); polycystic ovary disease (see Prelevic, G. M., et al., Metabolism Clinical and Experimental, 41, Suppl. 2, pp 76-79, 1992); upper gastrointestinal bleeding (see Jenkins, S. A., et al., Gut., 33, pp. 404-407, 1992 and Arrigoni, A., et al., American Journal of Gastroenterology, 87, p. 1311, (abs. 275), 1992); pancreatic pseudocysts and ascites (see Hartley, J. E., et al., J. Roy. Soc. Med., 85, pp. 107-108, 1992); leukemia (see Santini, et al., 78, (Suppl. 1), p. 429A (Abs. 1708), 1991); meningioma (see Koper, J. W., et al., J. Clin. Endocr. Metab., 74, pp. 543-547, 1992); and cancer cachexia (see Bartlett, D. L., et al., Surg. Forum., 42, pp. 14-16, 1991).

Other indications associated with activation of the SRIF receptor subtypes are inhibition of insulin and/or glucagon and more particularly diabetes mellitus, angiopathy, proliferative retinopathy, dawn phenomenon and Nephropathy; inhibition of gastric acid secretion and more particularly peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis, treatment of inflammatory disorders such as arthritis; retinopathy; chronic allograft rejection; angioplasty; preventing graft vessel and gastrointestinal bleeding.

It is preferred to have an analog which is selective for the specific SRIF receptor subtype or subtypes responsible for the desired biological response, thus, reducing interaction with other receptor subtypes which could lead to undesirable side effects. Further, because of the short half-life of native SRIF, various SRIF analogs have been developed, e.g., for the treatment of acromegaly. (Raynor, et al., Molecular Pharmacol. 43:838 (1993)) The development of potent, smaller SRIF agonists led to the discovery of differing affinities of the various truncated ligands for the different subtypes. It appears that $Trp^8$-$Lys^9$ residue often is present in ligands that are recognized by the receptor. The $Trp^8$-$Lys^9$ residue forms part of a β-bend which is usually stabilized via substitution of D- for L-Trp, cyclization of the backbone, a disulfide bridge, or all constraints. One unintended consequence of such structural simplification, carried out before the discovery of multiple receptor subtypes, was the loss of broad spectrum binding affinity. This is typified by the high type 2 but low type 1, 3, 4, and 5 affinities of peptides in the OCTREOTIDE® series. Thus, the many basic biological studies with this type of analogue failed to detect effects mediated by all but one of the SRIF receptor subtypes.

We have discovered that peptide backbone constraint can be introduced by N-alkylation. This modification largely restricts the affected residue and the amino acid preceding it to an extended conformation and additionally blocks potential intramolecular hydrogen bonding sites and also proteolytic enzyme cleavage sites thus potentially enhancing pharmacokinetic properties of a peptide. Only a few N-methyl amino acids are commercially available and their synthesis is tedious. However, in another aspect of the present invention, we have discovered a procedure to N-methylate truncated SRIF analogues at every amino acid residue using the solid-phase procedure, adopted from that reported by Miller and Scanlan, (*J. Am. Chem. Soc.* 1997, 119, 2301-2302).

In one aspect the invention relates to a peptide according to formula (I):

$$A^1\text{-cyclo}[Cys\text{-}A^2\text{-}D\text{-Trp-}A^3\text{-}A^4\text{-}Cys]\text{-}A^5\text{-}Y^1,\qquad (I)$$

wherein:

$A^1$ is an optionally substituted D- or L-aromatic α-amino acid or optionally substituted D- or L-cyclo($C_{3-6}$)alkylalanine;

$A^2$ is an optionally substituted aromatic α-amino acid or optionally substituted cyclo($C_{3-6}$)alkylalanine;

$A^3$ is Lys or Orn;

$A^4$ is β-Hydroxyvaline, Ser, hSer, or Thr;

$A^5$ is β-Hydroxyvaline, Ser, hSer, or Thr; and $Y^1$ is OH, $NH_2$ or $NHR^1$, where $R^1$ is ($C_{1-6}$)alkyl;

wherein each said optionally substituted aromatic α-amino acid and each said optionally substituted cyclo($C_{3-6}$)alkylalanine is optionally substituted with one or more substituents each independently selected from the group consisting of halogen, $NO_2$, OH, CN, ($C_{1-6}$)alkyl, ($C_{2-6}$)alkenyl, ($C_{2-6}$)alkynyl, ($C_{1-6}$)alkoxy, Bzl, O-Bzl, and $NR^9R^{10}$, where $R^9$ and $R^{10}$ each is independently H or ($C_{1-6}$) alkyl; and wherein the amine nitrogen of one or more peptide bond is substituted with a methyl group; and further provided that said compound is not D-Phe-cyclo[Cys-Phe-D-Trp-Lys-(N-Me-Thr)-Cys]-Thr-$NH_2$;

or a pharmaceutically acceptable salt thereof.

A preferred group of compounds of formula (I) are those compounds wherein:

$A^1$ is Phe, D-Phe, Tyr, D-Tyr, β-Nal, D-β-Nal, Cha or D-Cha;

$A^2$ is Phe, Tyr, β-Nal or Cha; and $Y^1$ is OH or $NH_2$;

or a pharmaceutically acceptable salt thereof.

A preferred group of compounds of the immediately foregoing group of compounds are those compounds wherein $A^1$ is D-Phe or Tyr; or wherein $A^2$ is Phe; or wherein $A^3$ is Lys; or wherein $A^4$ is Thr; or wherein $A^5$ is Thr; or a pharmaceutically acceptable salt thereof.

In a still more preferred embodiment the invention features a compound of formula (I) wherein said compound is according to the formula:

D-Phe-{(N-Me-Cys)-Phe-D-Trp-Lys-Thr-Cys}-Thr-$NH_2$;

D-Phe-cyclo{Cys-(N-Me-Phe)-D-Trp-Lys-Thr-Cys}-Thr-$NH_2$;

D-Phe-{Cys-Phe-(N-Me-D-Trp)-Lys-Thr-Cys}-Thr-$NH_2$;

D-Phe-{Cys-Phe-D-Trp-(N-Me-Lys)-Thr-Cys}-Thr-$NH_2$;

D-Phe-cyclo{Cys-Phe-D-Trp-Lys-Thr-(N-Me-Cys)}-Thr-$NH_2$;

D-Phe-cyclo{Cys-Phe-D-Trp-Lys-Thr-Cys}-(N-Me-Thr)-$NH_2$;

Tyr-{(N-Me-Cys)-Phe-D-Trp-Lys-Thr-Cys}-Thr-$NH_2$;

Tyr-{Cys-(N-Me-Phe)-D-Trp-Lys-Thr-Cys}-Thr-$NH_2$;

Tyr-{Cys-Phe-(N-Me-D-Trp)-Lys-Thr-Cys}-Thr-$NH_2$;

Tyr-{Cys-Phe-D-Trp-(N-Me-Lys)-Thr-Cys}-Thr-$NH_2$;

Tyr-{Cys-Phe-D-Trp-Lys-(N-Me-)Thr-Cys}-Thr-$NH_2$;

Tyr-{Cys-Phe-D-Trp-Lys-Thr-(N-Me-Cys)}-Thr-$NH_2$; or

Tyr-{Cys-Phe-D-Trp-Lys-Thr-Cys}-(N-Me-Thr)-$NH_2$;

or a pharmaceutically acceptable salt thereof.

In another aspect, the invention features a compound according to formula (II), $$\begin{array}{c}R_1\\ \diagdown\\ A^1-A^2-A^3-D\text{-Trp-Lys-}A^6-A^7-A^8-R_3\\ \diagup\\ R_2\end{array}\qquad (II)$$

wherein $A^1$ is a D- or L-isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is $CH_3$, Cl, Br, F, OH, $OCH_3$ or $NO_2$;

$A^2$ is Ala, Leu, Ile, Val, Nle, Phe, β-Nal, β-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;

$A^3$ is β-Ala, Trp, Phe, β-Nal, 2,4-dichloro-Phe, pentafluoro-Phe, o-X-Phe, or p-X-Phe, wherein X is $CH_3$, Cl, Br, F, OH, $OCH_3$ or $NO_2$;

$A^6$ is Val, Ala, Leu, Ile, Nle, Thr, Abu, or Ser;

$A^7$ is Ala, Leu, Ile, Val, Nle, Phe, β-Nal, β-Ala, Trp, 2,4-dichloro-Phe, pentafluoro-Phe, o-X-Phe, or p-X-Phe, wherein X is $CH_3$, CL, Br, F, OH, $OCH_3$ or $NO_2$;

$A^8$ is a D- or L-isomer of Ala, Leu, Ile, Val, Nle, Thr, Ser, Phe, β-Nal, β-Ala, Trp, 2,4-dichloro-Phe, pentafluoro-Phe, p-X-Phe, or o-X-Phe, wherein X is $CH_3$, Cl, Br, F, OH, $OCH_3$ or $NO_2$;

each $R_1$ and $R_2$, independently, is H, lower acyl or lower alkyl; and $R_3$ is OH or $NH_2$; wherein the amine nitrogen of one or more amide peptide bond is substituted with a methyl group;

provided that at least one of $A^1$ and $A^8$ and one of $A^2$ and $A^7$ must be an aromatic amino acid; and that $A^1$, $A^2$, $A^7$ and $A^8$ cannot all be aromatic amino acids;

or a pharmaceutically acceptable salt thereof.

In one embodiment the invention features a compound according to formula (II) wherein said compound is selected from the list consisting of:

H-D-Phe-p-chloro-Phe-Tyr-D-Trp-Lys-Thr-Phe-Thr-NH$_2$;
H-D-Phe-p-NO$_2$-Phe-Tyr-D-Trp-Lys-Val-Phe-Thr-NH$_2$;
H-D-Nal-p-chloro-Phe-Tyr-D-Trp-Lys-Val-Phe-Thr-NH$_2$;
H-D-Phe-Phe-Phe-D-Trp-Lys-Thr-Phe-Thr-NH$_2$;
H-D-Phe-Phe-Tyr-D-Trp-Lys-Val-Phe-Thr-NH$_2$;
H-D-Phe-p-chloro-Phe-Tyr-D-Trp-Lys-Val-Phe-Thr-NH$_2$; and
H-D-Phe-Ala-Tyr-D-Trp-Lys-Val-Ala-β-D-Nal-NH$_2$;

wherein the amine nitrogen of one or more peptide bond is substituted with a methyl group;

or a pharmaceutically acceptable salt thereof.

In another embodiment the invention features a peptide selected from the list of peptides, denoted "group III", consisting of:

D-β-Nal-Cys-Tyr-D-Trp-Lys-Thr-Cys-Thr-NH$_2$;
D-Phe-Cys-Phe-D-Trp-Lys-Thr-Cys-β-Nal-NH$_2$;
D-Phe-Cys-Tyr-D-Trp-Lys-Thr-Cys-β-Nal-NH$_2$;
D-β-Nal-Cys-Phe-D-Trp-Lys-Thr-Cys-Thr-NH$_2$;
D-Phe-Cys-Tyr-D-Trp-Lys-Thr-Pen-Thr-NH$_2$;
D-Phe-Cys-Phe-D-Trp-Lys-Thr-Pen-Thr-NH$_2$;
D-Phe-Cys-Tyr-D-Trp-Lys-Thr-Pen-Thr-OH;
D-Phe-Cys-Phe-D-Trp-Lys-Thr-Pen-Thr-OH;
Gly-Pen-Phe-D-Trp-Lys-Thr-Cys-Thr-OH;
Phe-Pen-Tyr-D-Trp-Lys-Thr-Cys-Thr-OH;
Phe-Pen-Phe-D-Trp-Lys-Thr-Pen-Thr-OH;
H-D-Phe-Cys-Phe-D-Trp-Lys-Thr-Cys-Thr-OH;
H-D-Phe-Cys-Phe-D-Trp-Lys-Thr-Cys-Thr-NH$_2$;
H-D-Trp-Cys-Tyr-D-Trp-Lys-Val-Cys-Thr-NH$_2$;
H-D-Trp-Cys-Phe-D-Trp-Lys-Thr-Cys-Thr-NH$_2$;
H-D-Phe-Cys-Tyr-D-Trp-Lys-Val-Cys-Thr-NH$_2$;
H-D-Phe-Cys-Tyr-D-Trp-Lys-Val-Cys-Trp-NH$_2$;
H-D-Phe-Cys-Tyr-D-Trp-Lys-Val-Cys-Thr-NH$_2$;
Ac-D-Phe-Lys*-Tyr-D-Trp-Lys-Val-Asp-Thr-NH$_2$ (an amide bridge formed between Lys* and Asp);
Ac-hArg(Et)$_2$-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NH$_2$;
Ac-D-hArg(Bu)-Gly-Cys-Phe-D-Trp-Lys-Thr-Cys-Thr-NH$_2$;
Ac-D-hArg(Et)$_2$-Cys-Phe-D-Trp-Lys-Thr-Cys-Thr-NH$_2$;
Ac-L-hArg(Et)$_2$-Cys-Phe-D-Trp-Lys-Thr-Cys-Thr-NH$_2$;
Ac-D-hArg(CH$_2$CF$_3$)$_2$-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys-Thr-Cys-Phe-NH$_2$;
Ac-D-hArg(CH$_2$CF$_3$)$_2$-Gly-Cys-Phe-D-Trp-Lys-Thr-Cys-Thr-NHEt;
Ac-L-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-Gly-Cys-Phe-D-Trp-Lys(Me)-Thr-Cys-Thr-NH$_2$;
Ac-D-hArg(CH$_2$CF$_3$)$_2$-Gly-Cys-Phe-D-Trp-Lys(Me)-Thr-Cys-Thr-NHEt;
Ac-hArg(CH$_3$; hexyl)-Gly-Cys-Phe-D-Trp-Lys-Thr-Cys-Thr-NH$_2$;
H-hArg(hexyl$_2$)-Gly-Cys-Phe-D-Trp-Lys-Thr-Cys-Thr-NH$_2$;
Ac-D-hArg(Et)$_2$-Gly-Cys-Phe-D-Trp-Lys-Thr-Cys-Thr-NHEt;
Ac-D-hArg(Et)$_2$-Gly-Cys-Phe-D-Trp-Lys-Thr-Cys-Phe-NH$_2$;
Propionyl-D-hArg(Et)$_2$-Gly-Cys-Phe-D-Trp-Lys(iPr)-Thr-Cys-Thr-NH$_2$;
Ac-D-β-Nal-Gly-Cys-Phe-D-Trp-Lys-Thr-Cys-Gly-hArg(Et)$_2$-NH$_2$;
Ac-D-Lys(iPr)-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Thr-NH$_2$;
Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$;
Ac-D-hArg(Et)$_2$-D-hArg(Et)$_2$-Gly-Cys-Phe-D-Trp-Lys-Thr-Cys-Thr-NH$_2$;
Ac-Cys-Lys-Asn-4-Cl-Phe-Phe-D-Trp-Lys-Thr-Phe-Thr-Ser-D-Cys-NH$_2$;
Bmp-Tyr-D-Trp-Lys-Val-Cys-Thr-NH$_2$;
Bmp-Tyr-D-Trp-Lys-Val-Cys-Phe-NH$_2$;
Bmp-Tyr-D-Trp-Lys-Val-Cys-p-Cl-Phe-NH$_2$;
Bmp-Tyr-D-Trp-Lys-Val-Cys-β-Nal-NH$_2$;
H-D-β-Nal-Cys-Tyr-D-Trp-Lys-Val-Cys-Thr-NH$_2$;
H-D-Phe-Cys-Tyr-D-Trp-Lys-Abu-Cys-Thr-NH$_2$;
H-D-Phe-Cys-Tyr-D-Trp-Lys-Abu-Cys-β-Nal-NH$_2$;
H-pentafluoro-D-Phe-Cys-Tyr-D-Trp-Lys-Val-Cys-Thr-NH$_2$;
Ac-D-β-Nal-Cys-pentafluoro-Phe-D-Trp-Lys-Val-Cys-Thr-NH$_2$;
H-D-β-Nal-Cys-Tyr-D-Trp-Lys-Val-Cys-β-Nal-NH$_2$;
H-D-Phe-Cys-Tyr-D-Trp-Lys-Val-Cys-β-Nal-NH$_2$;
H-D-β-Nal-Cys-Tyr-D-Trp-Lys-Abu-Cys-Thr-NH$_2$;
H-D-p-Cl-Phe-Cys-Tyr-D-Trp-Lys-Abu-Cys-Thr-NH$_2$;
Ac-D-p-Cl-Phe-Cys-Tyr-D-Trp-Lys-Abu-Cys-Thr-NH$_2$;
H-D-Phe-Cys-β-Nal-D-Trp-Lys-Val-Cys-Thr-NH$_2$;
H-D-Phe-Cys-Tyr-D-Trp-Lys-Cys-Thr-NH$_2$;
cyclo[Pro-Phe-D-Trp-Lys(Me)-Thr-Phe];
cyclo[Pro-Phe-D-Trp-Lys(Me)-Thr-Phe];
cyclo(Pro-Phe-D-Trp-Lys-Thr-N-Me-Phe);
cyclo[Ala(Me)-Tyr-D-Trp-Lys-Thr-Phe];
cyclo[Pro-Tyr-D-Trp-Lys-Thr-Phe];
cyclo[Pro-Phe-D-Trp-Lys-Thr-Phe];
cyclo[Pro-Phe-L-Trp-Lys-Thr-Phe];
cyclo[Pro-Phe-D-Trp(F)-Lys-Thr-Phe];
cyclo[Pro-Phe-Trp(F)-Lys-Thr-Phe];
cyclo[Pro-Phe-D-Trp-Lys-Ser-Phe];
cyclo[Pro-Phe-D-Trp-Lys-Thr-p-Cl-Phe];
cyclo[D-Ala-D-Phe(Me)-D-Thr-D-Lys-Trp-D-Phe];
cyclo[D-Ala-D-Phe(Me)-D-Val-Lys-D-Trp-D-Phe];
cyclo[D-Ala-D-Phe(Me)-D-Thr-Lys-D-Trp-D-Phe];
cyclo[-Abu-D-Phe(Me)-D-Val-Lys-D-Trp-D-Tyr];
cyclo[Pro-Tyr-D-Trp-t-4-AchxAla-Thr-Phe];
cyclo[Pro-Phe-D-Trp-t-4-AchxAla-Thr-Phe];
cyclo[Ala(Me)-Tyr-D-Trp-Lys-Val-Phe];
cyclo[Ala(Me)-Tyr-D-Trp-t-4-AchxAla-Thr-Phe];
cyclo[Pro-Tyr-D-Trp-4-Amphe-Thr-Phe];
cyclo[Pro-Phe-D-Trp-4-Amphe-Thr-Phe];
cyclo[Ala(Me)-Tyr-D-Trp-4-Amphe-Thr-Phe];
cyclo[Asn-Phe-Phe-D-Trp-Lys-Thr-Phe-Gaba];
cyclo[Asn-Phe-Phe-D-Trp-Lys-Thr-Phe-Gaba-Gaba];
cyclo[Asn-Phe-D-Trp-Lys-Thr-Phe];
cyclo[Asn-Phe-Phe-D-Trp-Lys-Thr-Phe-NH(CH$_2$)$_4$CO];
cyclo[Asn-Phe-Phe-D-Trp-Lys-Thr-Phe-β-Ala];
cyclo[Asn-Phe-Phe-D-Trp-Lys-Thr-Phe-D-Glu]-OH;
cyclo[Phe-Phe-D-Trp-Lys-Thr-Phe];
cyclo[Phe-Phe-D-Trp-Lys-Thr-Phe-Gly];
cyclo[Phe-Phe-D-Trp-Lys-Thr-Phe-Gaba];

cyclo[Asn-Phe-Phe-D-Trp-Lys-Thr-Phe-Gly];
cyclo[Asn-Phe-Phe-D-Trp(F)-Lys-Thr-Phe-Gaba];
cyclo[Asn-Phe-Phe-D-Trp(NO₂)-Lys-Thr-Phe-Gaba];
cyclo[Asn-Phe-Phe-Trp(Br)-Lys-Thr-Phe-Gaba];
cyclo[Asn-Phe-Phe-D-Trp-Lys-Thr-Phe(I)-Gaba];
cyclo[Asn-Phe-Phe-D-Trp-Lys-Thr-Tyr(tBu)-Gaba];
cyclo[Bmp-Lys-Asn-Phe-Phe-D-Trp-Lys-Thr-Phe-Thr-Pro-Cys]-OH;
cyclo[Bmp-Lys-Asn-Phe-Phe-D-Trp-Lys-Thr-Phe-Thr-Pro-Cys]-OH;
cyclo[Bmp-Lys-Asn-Phe-Phe-D-Trp-Lys-Thr-Phe-Thr-Tpo-Cys]-OH;
cyclo[Bmp-Lys-Asn-Phe-Phe-D-Trp-Lys-Thr-Phe-Thr-MeLeu-Cys]-OH;
cyclo[Phe-Phe-D-Trp-Lys-Thr-Phe-Phe-Gaba];
cyclo[Phe-Phe-D-Trp-Lys-Thr-Phe-D-Phe-Gaba];
cyclo[Phe-Phe-D-Trp(F)-Lys-Thr-Phe-Phe-Gaba];
cyclo[Asn-Phe-Phe-D-Trp-Lys(Ac)-Thr-Phe-NH—(CH₂)₃—CO];
cyclo[Lys-Phe-Phe-D-Trp-Lys-Thr-Phe-Gaba];
cyclo[Lys-Phe-Phe-D-Trp-Lys-Thr-Phe-Gaba];
cyclo[Orn-Phe-Phe-D-Trp-Lys-Thr-Phe-Gaba];
H-Cys-Phe-Phe-D-Trp-Lys-Thr-Phe-Cys-NH₂;

U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,190 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Application 0 363 589 A2 (1990);
EP Patent No. 0 389 180 (1990);
EP Application No. 0 505 680 (1982);
EP Application No. 0 083 305 (1982);
EP Application No. 0 030 920 (1980);

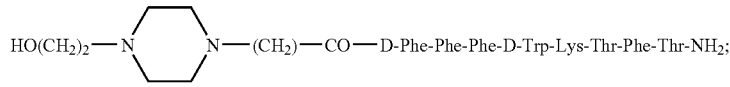

and

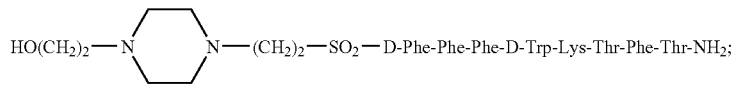

or a pharmaceutically acceptable salt thereof, wherein a disulfide bond exists in those compounds having two Cys residues and where the amine nitrogen of one or more peptide bond is substituted with a methyl group.

In a further aspect the present invention features SRIF agonists comprising the N-methylated analogs of the SRIF agonists covered by formulae or those specifically recited in the publications set forth below.

EP Application No. P5 164 EU (Inventor: G. Keri);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13-19, 1992, Interlaken, Switzerland;
U.S. Pat. No. 6,001,801 (1999);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987)
U.S. Pat. No. 4,650,787 (1987);
U.S. Pat. No. 4,603,120 (1986);
U.S. Pat. No. 4,585,755 (1986);
EP Application 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
PCT Application No. WO 97/01579 (1997);
PCT Application No. WO 91/18016 (1991);
PCT Application No. WO 91/09056 (1991);
PCT Application No. WO 90/12811 (1990);
PCT Application No. WO 88/05052 (1988);
U.K. Application No. GB 2,095,261 (1981); and
French Application No. FR 2,522,655 (1983).

The compounds of formula (I), formula (II) and group (III) of the instant application are useful for the same uses as SRIF, dependent upon the binding specificity or lack thereof, as may be determined by the binding assays described herein.

Thus in another aspect the invention is featured a method of binding one or more of human somatostatin subtype receptors-1, -2, -3, -4 and -5, which comprises the step of administering one or more compounds of formula (I) and/or formula (II) and/or group (III), or a pharmaceutically acceptable salt(s) of such compound or compounds, to a recipient in need thereof.

In a preferred embodiment of the immediately foregoing method is featured a method of eliciting a somatostatin agonist effect, which comprises the step of administering one or more compounds of formula (I) and/or formula (II) and/or group (III), or a pharmaceutically acceptable salt(s) of such compound or compounds, to a recipient in need thereof.

In a more preferred embodiment of the immediately foregoing method is featured a method of treating a disease or condition in a human or other animal in need thereof, which comprises administering one or more compounds of formula (I) and/or formula (II) and/or group (III), or a pharmaceutically acceptable salt(s) of such compound or compounds, to said human or other animal, wherein said disease or condition is selected from the group consisting of Cushings Syndrome, gonadotropinoma, hyperparathyroidism, Paget's disease, VIPoma, nesidioblastosis, hyperinsulinism, gastrinoma, Zollinger-Ellison Syndrome, hypersecretory diarrhea related to AIDS and other conditions, irritable bowel syndrome, pancreatitis, Crohn's Disease, systemic sclerosis, thyroid cancer, psoriasis, hypotension, panic attacks, sclerodoma, small bowel obstruction, gastroesophageal reflux, duodenogastric reflux, Graves' Disease, polycystic ovary disease, upper gastrointestinal bleeding, pancreatic pseudocysts, pancreatic ascites, leukemia, meningioma, cancer cachexia, acromegaly, restenosis, hepatoma, lung cancer, melanoma, inhibiting the accelerated growth of a solid tumor, decreasing body weight, treating insulin resistance, Syndrome X, prolonging the survival of pancreatic cells, fibrosis, hyperlipidemia, hyperamylinemia, hyperprolactinemia and prolactinomas.

With the exception of the N-terminal amino acid, all abbreviations (e.g., Phe for $A^1$) of amino acids in this disclosure stand for the structure of —NH—CH(R)—CO—, wherein R in the immediately foregoing formula is the side chain of an amino acid (e.g., $CH_3$ for Ala). For the N-terminal amino acid, the abbreviation stands for the structure of $(R^1R^2)$—N—CH(R)—CO—, wherein R is a side chain of an amino acid and $R^1$ and $R^2$ are as defined herein.

The nomenclature for the somatostatin receptor subtypes is in accordance with the recommendations of IUPHAR, in which SSTR-4 refers to the receptor originally cloned by Bruno et al., and SSTR-5 refers to the receptor cloned by O'Carroll et al. Abbreviations of the common amino acids are in accordance with the recommendations of IUPAC-IUB. The following are abbreviations of certain α-amino acids as may appear herein:

| | |
|---|---|
| Abu = | α-ammobutyric acid |
| Aib = | α-aminoisobutyric acid; |
| Ala = | alanine; |
| β-Ala = | β-(3-pyridyl)-alanine; |
| Ala(Me) = | N-methyl alanine; |
| AchxAla = | aminocyclohexylalanine; |
| Amp = | 4-amino-phenylalanine; |
| Arg = | arginine; |
| hArg(Bu) = | N-guanidino-(butyl)-homoarginine; |
| hArg(CH$_2$CF$_3$)$_2$ = | N,N'=guanidine-bis-(2,2,2,-trifluoroethyl)-homo-arginine; |
| hArg(CH$_3$;hexyl) = | N,N'-guanidino-(methyl, hexyl)-homoarginine; |
| hArg(Et)$_2$ = | N,N'-guanidino-(dimethyl)-homoarginine; |
| hArg(hexyl$_2$) = | N,N'-guanidino-(dihexyl)-homoarginine; |
| Asp = | aspartic acid; |
| Ava = | 5-aminovaleric acid; |
| Bmp = | β-mercaptopropionyl; |
| Cha = | cyclohexylalanine; |
| Cys = | cysteine; |
| Gaba = | γaminobutyric acid; |
| Glu = | glutamic acid; |
| Gln = | glutamine; |
| Gly = | glycine; |
| His = | histidine; |
| Ile = | isoleucine; |
| Leu = | leucine; |
| Leu(Me) = | N-methyl leucine; |
| Lys = | lysine; |
| Lys(Ac) = | N-ε-acetyl-L-lysine; |
| Lys(iPr) = | N-isopropyllysine; |
| Lys(Me) = | N-methyllysine; |
| Met = | methionine; |
| β-Nal = | β-(2-naphthyl)alanine; |
| Nle = | norleucine; |
| Nva = | norvaline; |
| Orn = | ornithine; |

-continued

| | |
|---|---|
| Pal = | β-(3-pyridinyl)alanine; |
| Pen = | pencillamine; |
| Phe = | phenylalanine; |
| 4-Cl—Phe = | (4-chlorophenyl)alanine; |
| Q-chloro-Phe = | (p-chlorophenyl)alanine; |
| Phe(I) = | 4-iodo-phenyl)alanine; |
| Phe(Me) = | N-methyl phenylalanine; |
| Q-NO$_2$—Phe = | (p-nitrophenyl)alanine; |
| 2,4-dichloro-Phe = | β-(2,4-dichlorophenyl)alanine; |
| pentafluoro-Phe = | β-(2,3,4,5,6-pentaflurophenyl)alanine; |
| AmPhe = | aminomethylphenylalanine; |
| Pro = | proline; |
| Ser = | serine; |
| hSer = | homoserine; |
| Thr = | threonine; |
| Tpo = | 4-thioproline; |
| Trp = | tryptophan; |
| Trp(Br) = | 5-bromo-tryptophan; |
| Trp(F) = | 5-fluoro-tryptophan; |
| Trp(NO$_2$) = | 5-nitro-tryptophan; |
| Tyr = | tyrosine; |
| Tyr(tBu) = | t-butyl-tyrosine; and |
| Val = | valine. |

Additional abbreviations include:

DBU, 1,8-diazabicyclo[5.4.0]undec-7-ene;

DCM, dichloromethane;

DIC, dicyclohexylcarbodiimide;

DIEA, diisopropyethylamine;

DMF, dimethylformamide;

MTBD, 1,3,4,6,7,8-Hexahydro-1-methyl-2H-pyrimido[1,2-a]pyrimidine;

NPS, 2-nitrophenylsulfonyl;

TBTU, O-Benzotri-azol-1-yl-N,N,N',N'-tetramethyluronium tetrafluoroborate; and

TFA, trifluoroacetic acid.

The amine nitrogen of peptide bond which has been substituted with a methyl group for a particular compound is indicated in the formula as follows: (N-Me-amino acid). An amino acid which has been substituted with a methyl group, in contrast, is indicated as follows: amino acid(Me). For example, in the claimed compound Tyr-{Cys-Phe-D-Trp-(N-Me-Lys)-Thr-Cys}-Thr-NH$_2$, the amine nitrogen of the peptide bond between D-tryptophan in the $4^{th}$ position and lysine in the $5^{th}$ has been substituted with a methyl group whereas in the claimed compound Ac-D-hArg(CH$_2$CF$_3$)$_2$-Gly-Cys-Phe-D-Trp-Lys(Me)-Thr-Cys-Thr-NH$_2$, a hydrogen of the amino group found in the side chain of the lysine residue in the $6^{th}$ position has been substituted with a methyl group.

A compound of the present invention or pharmaceutically acceptable salt thereof can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 25 µg/kg/day to 100 mg/kg/day of body weight daily are administered as a single dose or divided into multiple doses to humans and other animals, e.g., mammals, to obtain the desired therapeutic effect.

A preferred general dosage range is 250 µg/kg/day to 5.0 mg/kg/day of body weight daily which can be administered as a single dose or divided into multiple doses.

Further, a compound of the present invention or pharmaceutically acceptable salt thereof can be administered in a sustained release composition such as those described in the following patents. Among those formulations, 14-day or 28-day slow release formulations will be preferred. U.S. Pat. No. 5,672,659 teaches sustained release compositions comprising a peptide and a polyester. U.S. Pat. No. 5,595,760 teaches sustained release compositions comprising a peptide in a gelable form. U.S. Pat. No. 5,821,221 teaches polymeric sustained release compositions comprising a peptide and chitosan. U.S. Pat. No. 5,916,883 teaches sustained release compositions comprising a peptide and cyclodextrin. International Patent Application No. PCT/US99/01180, (publication no. WO 99/38536, Aug. 5, 1999), teaches absorbable sustained release compositions of a peptide. The contents of the foregoing patents and applications are incorporated herein by reference.

The use of immediate or of sustained release compositions depends on the type of indications targeted. If the indication consists of an acute or over-acute disorder, a treatment with an immediate form will be preferred over the same with a prolonged release composition. On the contrary, for preventive or long-term treatments, a prolonged release composition will generally be preferred.

DETAILED DESCRIPTION OF THE INVENTION

One skilled in the art can, based on the description herein, utilize the present invention to its fullest extent. The following specific embodiments are, therefore, to be construed as merely illustrations of the invention and is not meant to be construed as limiting the full scope of the invention.

Synthesis

4-Methylbenzhydrylamine hydrochloride resin (0.25 or 0.5 mequiv $g^{-1}$) was obtained from Advanced ChemTech Inc., Louisville, Ky. $N^\alpha$ tert-Butyloxycarbonyl (Boc) protected amino acids were purchased from Bachem Inc., Torrance, Calif., Advanced ChemTech Inc., and Synthetech Inc., Albany, Oreg. The reactive side-chains of the amino acids were masked with one of the following groups: Cys, 4-methylbenzyloxycarbonyl; Lys, 2-chlorobenzyloxycarbonyl; Thr, O-benzyl; Tyr, O-2,6-dichlorobenzyl. All reagents and solvents were ACS grade or better and were used without further purification.

Compounds of the present invention, e.g., compounds of formula (I) can be and were synthesized on 4-methylbenzhydrylamine functionalized, 1% cross-linked polystyrene resin (0.25 or 0.5 mequiv $g^{-1}$), in 0.25 mmol scale on an Advanced ChemTech (model 200) synthesizer, using the following protocol: deblocking, 40% TFA (2 min, 20 min); DCM wash cycle (three washes); neutralization, 10% DIEA (1 min, 5 min); DMF wash cycle; DCM wash cycle (two washes); double coupling; first with 1,3-diisopropyl carbodiimide esters (3 equiv.), 30 min in DCM; DCM wash (three washes); second coupling with preformed TBTU esters (3 equiv.), 90 min in DMF, with a catalytic amount of DIEA; DMF wash (one wash); DCM wash (three washes). Coupling reactions were monitored qualitatively with the ninhydrin test.

$N^\alpha$-Protection. After deblocking the amino group at the desired methylation site, the resin was suspended in DCM (20 mL). To this suspension, collidine (3 equiv.) and o-nitrobenzenesulfonyl chloride (3 equiv.) were added and the mixture was shaken using Advanced ChemTech (model 200) synthesizer for 2 h. Then the resin was subjected to DCM wash (2 washes) and DMF wash (3 washes). Protection was monitored qualitatively by the ninhydrin test.

$N^\alpha$-Methylation. The o-nitrobenzenesulfonamide protected resin was suspended in DMF (20 mL), to which MTBD (3 equiv.) and methyl 4-nitrobenzenesulfonate or dimethyl sulfate (for $Cys^{11}$) were added. The mixture was shaken using Advanced ChemTech (model 200) synthesizer for 0.5 h and the resin was subjected to DMF wash (4 washes).

$N^\alpha$-Me Deprotection. Once the desired residue was methylated, the resin was again suspended in DMF (20 mL). DBU (3 equiv.) and 2-mercaptoethanol (3 equiv.) were added to the suspension and the mixture was agitated for 0.5 h in Advanced ChemTech (model 200) synthesizer. Then the resin was thoroughly washed with DMF (5 washes).

Peptide Cleavage. The peptides were cleaved from the resin support with simultaneous side-chain deprotection by acidolysis using anhydrous hydrogen fluoride containing the scavenger anisole (~30% v/v) for 45 min at 0° C. The peptides were cyclized in 90% acetic acid (~600 mL) with a slight excess of $I_2$ (15 min). Excess $I_2$ was then removed by the addition of ascorbic acid.

Purification. The crude peptides were purified by preparative reverse phase-high performance liquid chromatography (RP-HPLC) on C-18 bonded silica gel using axial compression columns (Dynamax-300 Å, 5 or 8 μm, 21.4×250 mm). A linear gradient elution system at a flow rate of 20 mL min$^{-1}$ was employed: A; 0.1% TFA, B; 0.1% TFA in 80% MeCN, 20% B to 50% B at 1% min$^{-1}$. The separations were monitored by analytical RP-HPLC at 215 nm. The fractions containing the product were pooled, concentrated in vacuo and subjected to lyophilization. Each peptide was obtained as a fluffy white powder of constant weight by lyophilization from aqueous acetic acid. The purity of the final peptides was assessed at 215 nm by analytical RP-HPLC. Analytical RP-HPLCs were recorded using a Vydac C-18 support (4.6 ⊚250 mm, 5 Mm, 300 Å pore size, Liquid Separations Group). The linear gradient system was used at a flow rate of 1.5 mL min$^{-1}$: HPLC-1, A, 0.1% TFA; B, 0.1% TFA in 80% MeCN; 20% B to 50% B at 1% min$^{-1}$; HPLC-2, C, 5% MeCN in TEAP (0.1 M, pH 3); D, 20% C in MeCN, 10% D to 70% D at 1% min$^{-1}$. Column eluent was monitored at 215 nm. The retention time and purity of each peptide was assessed by the Rainin Dynamax HPLC Method Manager.

Amino Acid Analysis. The peptides were hydrolyzed in vacuo (110° C.; 20 h) in 4 M methanesulfonic acid containing 0.2% 3-(2-aminoethyl)indole (Pierce). Amino acid analyses were performed on the hydrolyzates following derivatization with o-phthalidaldehyde reagent (Sigma Chemical Co.) using an automatic HPLC system (Rainin Instrument Co.) fitted with a 100×4.6 mm, 3 μm C18 axial compression column with integral guard column (Microsorb AAAnalysis™, Type O; Rainin Instrument Co.) The derivatized primary amino acids were eluted using a binary gradient of buffer A; 0.10 M sodium acetate containing 4.5% v/v methanol and 0.5% v/v tetrahydrofuran at pH 7.2 and buffer B; methanol. The gradient sequence; 0% A at 0 min; 35% A at 16.5 min; 90% A at 30 min and 90% A at 33 min was used with a flow rate of 1.0 mL min$^{-1}$ at ambient temperature. Eluent was monitored at 340 nm and integrated by the Dynamax HPLC Method Manager (Rainin). Standard retention times were as follows: Asp, 6.6 min; Arg, 19.9 min; Trp, 25.4 min and Lys, 29.5 min. Each peptide of Table I produced the expected analytical results for the primary amino acids. Cysteine was not quantified.

Mass Spectrometry. Peptides were analyzed by matrix-assisted laser desorption/ionization time-of-flight mass spectrometry using a LaserMat 2000 mass spectrometer (Thermal Bioanalysis, San Jose, Calif.) using α-cyano-4-hydroxycinnamic acid as the matrix with Substance P (1348.7 Da) as an internal standard. In each case, the spectra consisted of a major M-H⊕ ion peak for the internal standard, the expected analyte M-H⊕⊕ peak, and a few peaks associated with the matrix (<500 Da). Mass values so derived for certain representative compounds of the instant invention are detailed in Table 1.

SRIF Analogue Inhibition of GH Release. Anterior pituitaries from adult male rats were collected and dispersed by a previously described trypsin/DNase method. (Murphy, W. A.; Taylor, J.; Moreau, J.-P. and Coy, D. H., *Peptide Res.* 1989, 2, 128-132.) The dispersed cells were diluted with sterile-filtered Dulbecco's modified Eagle medium (MEM, Gibco Laboratories, Grand Island, N.Y.), which was supplemented with 2.5% fetal calf serum (Gibco), 3% horse serum (Gibco), 10% fresh rat serum (stored on ice for no longer than 1 h) from the pituitary donors, 1% MEM nonessential amino acids (Gibco), gentamycin (10 ng mL$^{-1}$; Sigma) and nystatin (10,000 U mL$^{-1}$; Gibco). The cells were randomly plated at a density of approximately 200,000 cells/well (Costar cluster 24; Rochester Scientific Co., Rochester, N.Y.). The plated cells were maintained in the above Dulbecco's medium in a humidified atmosphere of 95% air/5% $CO_2$ at 37° C. for 4-5 days. In preparation for a hormone challenge, the cells were washed with medium 199 (Gibco, 3×1 mL). Each dose of a compound of this invention was tested in triplicate wells in a total volume of 1 mL medium 199 containing 1% BSA (fraction V; Sigma Chemical Co.). All wells contained growth hormone releasing hormone (1-29)$NH_2$ (GHRH(1-29)$NH_2$) (1 nM). After incubation in an air/carbon dioxide atmosphere (95/5%, 3 h at 37° C.), the medium was removed and stored at −20° C. until assayed for hormone content. Growth hormone in media was measured by a standard double antibody radioimmunoassay (RIA) using components generously supplied by Dr. A. F. Parlow at the National Hormone and Pituitary Program (NHHP) Torrance, Calif. Agonist $IC_{50}$'s were calculated using Sigmaplot (Jandel Scientific, San Rafael, Calif.). Values are expressed as the mean $IC_{50}$ (nM)±SEM from (n) separate dose-response curves.

Functional Expression of the Cloned Human Somatostatin Receptors. The genomic clones containing the human somatostatin receptors (hSSTR-1 to hSSTR-5) (Yamada, Y., et al. al., *Proc. Natl. Acad. Sci. USA.* 1992, 89, 251-255; Yasuda, K., et al., *J. Biol. Chem.* 1992, 267, 20422-20428; Yamada, Y., et al., *Mol. Pharmacol.* 1992, 42, 2136-2142; Rohrer, L., et al., *Proc. Natl. Acad. Sci. USA.* 1993, 90, 4196-4200.) were kindly provided by Dr. Graeme I. Bell of the University of Chicago. The hSSTR-1, hSSTR-2, hSSTR-3, hSSTR-4 and hSSTR-5 cDNAs were isolated as a 1,5-kb PstI-XmnI fragment, 1,7-kb BamHI-HindIII fragment, 2,0-kb NcoI-HindIII fragment, 1,4-kb NheI-NdeI fragment, and a 1,2-kb HindIII-XbaI fragment, respectively, each containing the entire coding region of the full-length receptors. These fragments were independently subcloned into the corresponding restriction endonuclease sites in the mammalian expression vector pCMV5, downstream from the human cytomegalovirus (CMV) promoter, to produce the expression plasmids pCMV5/hSSTR-1, pCMV5/hSSTR-2, pCMV5/hSSTR-3, pCMV5/hSSTR-4 and pCMV5/hSSTR-5. For transfection into CHO-K1 cells, a plasmid, pRSV-neo (American Type Culture Collection, Rockville, Md.), carrying the neomycin mammalian cell selectable marker was added.

Receptor Expression and Transfection. Transfections were performed by the calcium phosphate method. CHO-K1 cells were maintained in α-minimum essential medium (α-MEM; Gibco) supplemented with 10% fetal calf serum and transfected with each of the expression plasmids using calcium phosphate precipitation. Clones that had inherited the expression plasmid were selected in α-MEM supplemented with 500 μg mL$^{-1}$ of geneticin (G418; Gibco). Independent CHO-K1 clones were picked by glass-ring cloning and expanded in culture in the selective media. Membranes were prepared from the isolated clones and hSSTR expression was initially assessed for binding with [$^{125}$I]Tyr$^{11}$-SRIF and [$^{125}$I]MK-678 (for SSTR-2).

Radioligand Binding Assays. Cell membranes of the 5 cells types were obtained from homogenates (Polytron setting 6, 15 sec) of the corresponding CHO-K1 cells, in ice-cold Tris-HCl (50 mM) and centrifuged (39000 g, 10 min×2), with an intermediate resuspension in fresh buffer. The final pellets were resuspended in Tris-HCl (10 mM) for assay. Aliquots of the membranes were incubated (30 min at 37° C.) with 0.05 nM [$^{125}$I]Tyr$^{11}$-SRIF (types 1, 3, 4, 5) or [$^{125}$I]MK-678 (type 2) in 50 nM HEPES (pH 7.4) containing BSA (10 mg mL$^{-1}$); MgCl$_2$ (5 mM), Trasylol (200 kIU mL$^{-1}$), bacitracin (0.02 mg mL$^{-1}$), and phenylmethanesulfonyl fluoride (0.02 mg mL$^{-1}$). The final assay volume was 0.3 mL and incubations were terminated by rapid filtration through GF/C filters pre-soaked in 0.3% poly(ethylenimine) using a Brandel rapid filtration module. Each tube and filter was then washed with aliquots of cold buffer (3×5 mL).

Specific binding is defined as the total radioligand bound minus that bound in the presence of 1.0 μM SRIF. The following total radioligand binding and non-specific binding (nsb) values were typically obtained with these assay systems: hSSTR-1, 7000 cpm total versus 3500 cpm nsb; hSSTR-2, 9000 cpm total versus 1000 cpm nsb; hSSTR-3, 8000 cpm total versus 1000 cpm nsb; hSSTR-4, 6000 cpm total versus 3500 cpm nsb; and hSSTR-5, 7500 cpm total versus 3500 cpm nsb. The binding affinities are expressed as Ki values±SEM (nM) for each of the five receptor subtypes. Ki values derived for representative compounds of the instant invention are detailed in Table 2.

Molecular Modeling. All molecular modeling was performed on a Silicon Graphics Indigo$^2$ High Impact 10000 computer, using SYBYL 6.6 with the Kollman all atom force field. The PDB files for the three solution nuclear magnetic resonance (NMR) structures of the initial compound Sandostatin/OCTREOTIDE®; DPhe$^5$-c[Cys$^6$-Phe$^7$-DTrp$^8$-Lys$^9$-Thr$^{10}$-Cys$^{11}$]-Thr$^{12}$-ol (1SOC and 2SOC) were obtained from the PDB database. These structures were imported into SYBYL6.6 and mutated to form the N-methylated compounds based on Example 9. The Kollman partial atomic charges were loaded from the monomer dictionary. The structures were optimized by annealing the mutated residue and then by full energy minimization using the conjugate gradient algorithm to a final root mean square (rms) gradient of ≦0.01 Kcal mol.Å$^{-1}$. A distance-dependent dielectric function was employed together with the default settings for all the other minimization options.

Examples 9 and 18 were alkylated at every residue by a solid phase procedure whilst being assembled on methylbenzhydrylamine resin. After the tert-butoxycarbonyl (Boc) group was removed at the desired N-methylation site, the free amine of the resin bound peptide was protected using o-nitrobenzenesulfonyl chloride and collidine in dichloromethane. Then the amide N—H of o-nitrobenzenesulfonamide was selectively deprotonated by the strong, hindered, non-ionic base MTBD and methylated using methyl p-nitrobenzenesulfonate in DMF. The methylated sulfonamide was deprotected by β-mercaptoethanol and DBU in DMF and this reaction was easily followed by the appearance of bright yellow color in the solution, indicating the removal of o-nitrobenzenesulfonyl group from the resin bound peptide. Also, this deprotection was slower if the N-sulfonamide was not alkylated, thus capping the unalkylated peptide. The subsequent amino acid was coupled two times using TBTU/DIPEA instead of DIC.

The sequence (o-NBS)HN-Cys$^{11}$(4-MeZ)-Thr$^{12}$(OBzl)-®  could not be methylated using methyl o-nitrobenzenesulfonate. This problem was, however, circumvented by using dimethyl sulfate as a methylating agent instead of the bulky methyl o-nitrobenzenesulfonate.

The binding affinities (Kd, nM) of all SRIF analogues were determined using their concentration-dependent displacement of $^{125}$I-radiolabeled peptide ligands from membranes isolated from CHO cells transfected with the corresponding human somatostatin receptor. For reference, the binding affinities of SRIF-14 and SRIF-28 in the same system were used. SRIF-28 displays particularly high affinity for type 5 receptors compared to SRIF-14. Given the profound effect which the conformation and side-chain of the N-terminal amino acid has on the biological activities of this type of analogue, two series of base structure (compounds 9 and 18) were used for the present study—one containing a DPhe (analogue 9) and the other a Tyr residue (analogue 18) to give a total of 16 N-methylated analogues, the structures and physicochemical characteristics of which are given in Table 1.

The compounds of the present invention were synthesized as described above and/or as described in the various references cited herein.

TABLE 1

N-Methyl Analogue Structures and Analytical Data

| Ex. No. | Sequence A$^1$-cyclo{Cys-A$^2$-D-Trp-A$^3$-A$^4$-Cys}-A$^5$-Y$^1$ | Mass Spectrum (M − H$^+$) Calcd.$^a$ | Obsd.$^b$ | HPLC$^c$ (t$_{R-1}$)$^d$ | (t$_{R-1}$)$^e$ |
|---|---|---|---|---|---|
| 2 | D-Phe-cyclo[(N-Me-Cys-Phe-D-Trp-Lys-Thr-Cys]-Thr-NH$_2$ | 1047.3 | 1048.0 | 16.3 | 16.4 |
| 3 | D-Phe-cyclo[Cys-(N-Me-Phe-D-Trp-Lys-Thr-Cys]-Thr-NH$_2$ | 1047.3 | 1048.8 | 14.4 | 14.8 |
| 4 | D-Phe-cyclo[Cys-Phe-(N-Me-D-Trp)-Lys-Thr-Cys]-Thr-NH$_2$ | 1047.3 | 1047.3 | 16.6 | 17.3 |
| 5 | D-Phe-cyclo[Cys-Phe-D-Trp-(N-Me-Lys)-Thr-Cys]-Thr-NH$_2$ | 1047.3 | 1047.6 | 15.6 | 15.7 |
| 6 | D-Phe-cyclo[Cys-Phe-D-Trp-Lys-(N-Me-Thr)-Cys]-Thr-NH$_2$ | 1047.3 | 1047.8 | 9.4 | 9.4 |
| 7 | D-Phe-cyclo[Cys-Phe-D-Trp-Lys-Thr-(N-Me-Cys]-Thr-NH$_2$ | 1047.3 | 1047.8 | 13.2 | 12.1 |
| 8 | D-Phe-cyclo[Cys-Phe-D-Trp-Lys-Thr-Cys]-(N-Me-Thr)-NH$_2$ | 1047.3 | 1048.1 | 10.9 | 10.8 |
| 11 | Tyr-cyclo[(N-Me-Cys)-Phe-D-Trp-Lys-Thr-Cys]-Thr-NH$_2$ | 1063.3 | 1063.7 | 14.3 | 14.7 |
| 12 | Tyr-cyclo[Cys-(N-Me-Phe)-D-Trp-Lys-Thr-Cys]-Thr-NH$_2$ | 1063.3 | 1063.4 | 13.6 | 13.4 |
| 13 | Tyr-cyclo[Cys-Phe-(N-Me-D-Trp)-Lys-Thr-Cys]-Thr-NH$_2$ | 1063.3 | 1063.7 | 15.8 | 15.9 |
| 14 | Tyr-cyclo[Cys-Phe-D-Trp-(N-Me-Lys)-Thr-Cys)-Thr-NH$_2$ | 1063.3 | 1063.2 | 17.7 | 18.2 |

TABLE 1-continued

N-Methyl Analogue Structures and Analytical Data

| Ex. No. | Sequence $A^1$-cyclo{Cys-$A^2$-D-Trp-$A^3$-$A^4$-Cys}-$A^5$-$Y^1$ | Mass Spectrum (M – H$^+$) Calcd.$^a$ | Obsd.$^b$ | HPLC$^c$ $(t_{R-1})^d$ | $(t_{R-1})^e$ |
|---|---|---|---|---|---|
| 15 | Tyr-cyclo[Cys-Phe-D-Trp-Lys-(N-Me-Thr)-Cys]-Thr-NH$_2$ | 1063.3 | 1063.0 | 11.5 | 11.7 |
| 16 | Tyr-cyclo[Cys-Phe-D-Trp-Lys-Thr-(N-Me-Cys)]-Thr-NH$_2$ | 1063.3 | 1063.4 | 14.2 | 14.2 |
| 17 | Tyr-cyclo[Cys-Phe-D-Trp-Lys-Thr-Cys]-(N-Me-Thr)-NH$_2$ | 1063.3 | 1063.7 | 11.6 | 11.9 |

$^a$Theoretical molecular weight (M – H+, Da).
$^b$Observed molecular weight (M – H+, Da).
$^c$Reversed-phase HPLC (C-18, 5 µm, 4.6 × 250 mm, λ = 215 nm) retention times (min). Each compound was found to have a purity of >98% by HPLC.
$^d$HPLC Elution System: A; 0.1% TFA, B; 0.1% TFA in 80% MeCN, 20% B to 50% B at 1% min$^{-1}$ and 1.5 mL min$^{-1}$.
$^e$HPLC-2 elution system: C, 5% MeCN in TEAP (0.1 M, pH 3); D, 20% C in MeCN, 10% D to 70% D at 1% min$^{-1}$ and 1.5 mL min$^{-1}$.

TABLE 2

Binding Affinities ($K_d$) of Analogues Shown in Table 1 for Cloned Human sst$_{1-5}$ Receptors and Agonist Activity (IC$_{50}$) on Culture Rat Pituitary Cells

| Ex. No. | $K_d{}^a$ ± SEM (nM) | | | | | Agonist IC$_{50}$ ± SEM (n)$^b$ (nM) |
|---|---|---|---|---|---|---|
| | hsst$_1$ | hsst$_2$ | hsst$_3$ | hsst$_4$ | hsst$_5$ | |
| SRIF-14 | 2.0 ± 0.35 | 0.25 ± 0.03 | 1.2 ± 0.23 | 2.0 ± 0.25 | 1.4 ± 0.29 | 0.17 ± 0.054 |
| SRIF-28 | 1.9 ± 0.42 | 0.31 ± 0.06 | 1.3 ± 0.29 | 5.4 ± 2.5 | 0.4 ± 0.05 | 0.23 ± 0.052 |
| 2 | 378 ± 119 | 1.04 ± 0.18 | 13 ± 0.5 | >1,000 | 23.71 | 0.36 ± 0.19 (4) |
| 3 | >1,000 | 13.17 ± 3.85 | 830 ± 86 | >1,000 | 83.24 ± 25.8 | 7.29 ± 2.08 (2) |
| 4 | 1,200 | 23.5 ± 3.92 | 11.05 ± 1.03 | >1,000 | 0.61 ± 0.36 | 18.7 ± 8.1 (2) |
| 5 | 867 ± 102 | 1.84 ± 0.21 | 67.48 ± 10.02 | >1,000 | 8.41 ± 6.85 | 0.74 ± 0.14 (4) |
| 6 | >1,000 | >1,000 | >1,000 | >1,000 | >1,000 | nd$^c$ |
| 7 | 622 ± 172 | 56.23 ± 26.4 | 44.4 ± 8.36 | 574 | 28.42 ± 19.3 | nd$^c$ |
| 8 | >1,000 | 14.84 ± 1.53 | 124.3 ± 11.7 | 182 | 313 | 28.8 ± 8.0 (2) |
| 11 | 862 ± 162 | 8.96 ± 1.66 | 2.73 ± 2.43 | nd$^c$ | 114.0 | 11.9 ± 4.1 (2) |
| 12 | 653 ± 245 | 40.09 ± 3.79 | 94.20 ± 16.71 | nd$^c$ | 94.99 ± 22.0 | 103 ± 4.0 (2) |
| 13 | 1,000 | 120.4 ± 22.2 | 8.00 ± 0.9 | nd$^c$ | 50.38 ± 28.6 | nd$^c$ |
| 14 | 956 ± 43 | 14.25 ± 3.12 | 51.02 ± 6.93 | nd$^c$ | 629 ± 371 | 27.4 ± 14.1 (2) |
| 15 | 1,000 | 61.35 ± 6.95 | 440 ± 126 | 1,000 | 92.79 ± 0.7 | nd$^c$ |
| 16 | 1,255 | 56.23 ± 26.4 | 17.00 ± 2.75 | 321 | 16.89 | 41.2 ± 31.9 (2) |
| 17 | 611 ± 3.5 | 26.17 ± 10.3 | 535 ± 200 | 353 | 71.84 ± 15.5 | nd$^c$ |

$^a$Expressed as the mean ± SEM, single values indicate the results of one binding experiment.
$^b$Rat in vitro antagonist IC$_{50}$ (nM) versus SRIF (1.0 nM), expressed as the mean ± SEM of (n) separate dose response curves.
$^c$Not determined.
$^d$Not applicable.

It is to be understood that while the invention has been described in conjunction with the detailed description thereof, that the foregoing description is intended to illustrate and not to limit the scope of the invention. Other aspects, advantages, and modifications are within the claims. Also, the contents of each references cited herein is incorporated by reference in its entirety.

What is claimed is:

1. A somatostatin agonist compound wherein the compound is D-Phe-cyclo[(N-Me-Cys)-Phe-D-Trp-Lys-Thr-Cys]-Thr-NH$_2$ or a pharmaceutically acceptable salt thereof.

2. A somatostatin agonist compound wherein the compound is D-Phe-cyclo[Cys-(N-Me-Phe)-D-Trp-Lys-Thr-Cys]-Thr-NH$_2$ or a pharmaceutically acceptable salt thereof.

3. A somatostatin agonist compound wherein the compound is D-Phe-cyclo[Cys-Phe-(N-Me-D-Trp)-Lys-Thr-Cys]-Thr-NH$_2$ or a pharmaceutically acceptable salt thereof.

4. A somatostatin agonist compound wherein the compound is D-Phe-cyclo[Cys-Phe-D-Trp-(N-Me-Lys)-Thr-Cys]-Thr-NH$_2$ or a pharmaceutically acceptable salt thereof.

5. A somatostatin agonist compound wherein the compound is D-Phe-cyclo[Cys-Phe-D-Trp-Lys-Thr-(N-Me-Cys)]-Thr-NH$_2$ or a pharmaceutically acceptable salt thereof.

6. A somatostatin agonist compound wherein the compound is D-Phe-cyclo[Cys-Phe-D-Trp-Lys-Thr-Cys]-(N-Me-Thr)-NH$_2$ or a pharmaceutically acceptable salt thereof.

7. A somatostatin agonist compound wherein the compound is Tyr-cyclo[(N-Me-Cys)-Phe-D-Trp-Lys-Thr-Cys]-Thr-NH₂ or a pharmaceutically acceptable salt thereof.

8. A somatostatin agonist compound wherein the compound is Tyr-cyclo[Cys-(N-Me-Phe)-D-Trp-Lys-Thr-Cys]-Thr-NH₂ or a pharmaceutically acceptable salt thereof.

9. A somatostatin agonist compound wherein the compound is Tyr-cyclo[Cys-Phe-(N-Me-D-Trp)-Lys-Thr-Cys]-Thr-NH₂ or a pharmaceutically acceptable salt thereof.

10. A somatostatin agonist compound wherein the compound is Tyr-cyclo[Cys-Phe-D-Trp-(N-Me-Lys)-Thr-Cys]-Thr-NH₂ or a pharmaceutically acceptable salt thereof.

11. A somatostatin agonist compound wherein the compound is Tyr-cyclo[Cys-Phe-D-Trp-Lys-(N-Me-Thr)-Cys]-Thr-NH₂ or a pharmaceutically acceptable salt thereof.

12. A somatostatin agonist compound wherein the compound is Tyr-cyclo[Cys-Phe-D-Trp-Lys-Thr-(N-Me-Cys)]-Thr-NH₂ or a pharmaceutically acceptable salt thereof.

13. A somatostatin agonist compound wherein the compound is Tyr-cyclo[Cys-Phe-D-Trp-Lys-Thr-Cys]-(N-Me-Thr)-NH₂ or a pharmaceutically acceptable salt thereof.

14. A method of binding one or more of human somatostatin subtype receptors-1, -2, -3, -4 and -5, which comprises the step of administering a compound according to any one of claims 1-6 or 7-13, or a pharmaceutically acceptable salt thereof, to a recipient in need thereof.

15. A method of eliciting a somatostatin agonist effect, which comprises the step of administering a compound according to any one of claims 1-6 or 7-13, or a pharmaceutically acceptable salt thereof, to a recipient in need thereof.

16. A method of treating a disease or condition in a human or a mammal in need thereof, which comprises administering a compound according to any one of claims 1-6 or 7-13, or a pharmaceutically acceptable salt thereof, to said human or mammal, wherein said disease or condition is selected from the group consisting of Cushings Syndrome, gonadotropinoma, gastrinoma, Zollinger-Ellison Syndrome, hypersecretory diarrhea related to AIDS and other conditions, irritable bowel syndrome, pancreatitis, Crohn's Disease, systemic sclerosis, thyroid cancer, psoriasis, hypotension, panic attacks, sclerodoma, small bowel obstruction, gastroesophageal reflux, duodenogastric reflux, Graves' Disease, polycystic ovary disease, upper gastrointestinal bleeding, pancreatic pseudocysts, pancreatic ascites, leukemia, meningioma, cancer cachexia, acromegaly, restenosis, hepatoma, lung cancer, melanoma, inhibiting the accelerated growth of a solid tumor, decreasing body weight, treating insulin resistance, Syndrome X, prolonging the survival of pancreatic cells, fibrosis, hyperlipidemia, hyperamylinemia, hyperprolactinemia and prolactinomas.

17. A compound selected from the group consisting of:
D-β-Nal-Cys-Tyr-D-Trp-Lys-Thr-Cys-Thr-NH₂;
D-Phe-Cys-Phe-D-Trp-Lys-Thr-Cys-β-Nal-NH₂;
D-Phe-Cys-Tyr-D-Trp-Lys-Thr-Cys-β-Nal-NH₂;
D-β-Nal-Cys-Phe-D-Trp-Lys-Thr-Cys-Thr-NH₂;
D-Phe-Cys-Tyr-D-Trp-Lys-Thr-Pen-Thr-NH₂;
D-Phe-Cys-Phe-D-Trp-Lys-Thr-Pen-Thr-NH₂;
D-Phe-Cys-Tyr-D-Trp-Lys-Thr-Pen-Thr-OH;
D-Phe-Cys-Phe-D-Trp-Lys-Thr-Pen-Thr-OH;
Gly-Pen-Phe-D-Trp-Lys-Thr-Cys-Thr-OH;
Phe-Pen-Tyr-D-Trp-Lys-Thr-Cys-Thr-OH;
Phe-Pen-Phe-D-Trp-Lys-Thr-Pen-Thr-OH;
H-D-Phe-Cys-Phe-D-Trp-Lys-Thr-Cys-Thr-OH;
H-D-Trp-Cys-Tyr-D-Trp-Lys-Val-Cys-Thr-NH₂;
H-D-Trp-Cys-Phe-D-Trp-Lys-Thr-Cys-Thr-NH₂;
H-D-Phe-Cys-Tyr-D-Trp-Lys-Val-Cys-Thr-NH₂;
H-D-Phe-Cys-Tyr-D-Trp-Lys-Val-Cys-Trp-NH₂;
H-D-Phe-Cys-Tyr-D-Trp-Lys-Val-Cys-Thr-NH₂;
Ac-D-Phe-Lys*-Tyr-D-Trp-Lys-Val-Asp-Thr-NH₂ (an amide bridge is formed between Lys* and Asp);
Ac-hArg(Et)₂-Gly-Cys-Phe-D-Trp-Lys-Thr-Cys-Thr-NH₂;
Ac-D-hArg(Et)₂-Gly-Cys-Phe-D-Trp-Lys-Thr-Cys-Thr-NH₂;
Ac-D-hArg(Bu)-Gly-Cys-Phe-D-Trp-Lys-Thr-Cys-Thr-NH₂;
Ac-D-hArg(Et)₂-Cys-Phe-D-Trp-Lys-Thr-Cys-Thr-NH₂;
Ac-L-hArg(Et)₂-Cys-Phe-D-Trp-Lys-Thr-Cys-Thr-NH₂;
Ac-D-hArg(CH₂CF₃)₂-Cys-Phe-D-Trp-Lys-Thr-Cys-Thr-NH₂;
Ac-D-hArg(CH₂CF₃)₂-Gly-Cys-Phe-D-Trp-Lys-Thr-Cys-Thr-NH₂;
Ac-D-hArg(CH₂CF₃)₂-Gly-Cys-Phe-D-Trp-Lys-Thr-Cys-Phe-NH₂;
Ac-D-hArg(CH₂CF₃)₂-Gly-Cys-Phe-D-Trp-Lys-Thr-Cys-Thr-NHEt;
Ac-L-hArg(CH₂CF₃)₂-Gly-Cys-Phe-D-Trp-Lys-Thr-Cys-Thr-NH₂;
Ac-D-hArg(CH₂CF₃)₂-Gly-Cys-Phe-D-Trp-Lys(Me)-Thr-Cys-Thr-NH₂;
Ac-D-hArg(CH₂CF₃)₂-Gly-Cys-Phe-D-Trp-Lys(Me)-Thr-Cys-Thr-NHEt;
Ac-hArg(CH₃; hexyl)-Gly-Cys-Phe-D-Trp-Lys-Thr-Cys-Thr-NH₂;
H-hArg(hexyl₂)-Gly-Cys-Phe-D-Trp-Lys-Thr-Cys-Thr-NH₂;
Ac-D-hArg(Et)₂-Gly-Cys-Phe-D-Trp-Lys-Thr-Cys-Thr-NHEt;
Ac-D-hArg(Et)₂-Gly-Cys-Phe-D-Trp-Lys-Thr-Cys-Phe-NH₂;
Propionyl-D-hArg(Et)₂-Gly-Cys-Phe-D-Trp-Lys(iPr)-Thr-Cys-Thr-NH₂;
Ac-D-β-Nal-Gly-Cys-Phe-D-Trp-Lys-Thr-Cys-Gly-hArg(Et)₂-NH₂;
Ac-D-Lys(iPr)-Gly-Cys-Phe-D-Trp-Lys-Thr-Cys-Thr-NH₂;
Ac-D-hArg(CH₂CF₃)₂-D-hArg(CH₂CF₃)₂-Gly-Cys-Phe-D-Trp-Lys-Thr-Cys-Thr-NH₂;
Ac-D-hArg(CH₂CF₃)₂-D-hArg(CH₂CF₃)₂-Gly-Cys-Phe-D-Trp-Lys-Thr-Cys-Phe-NH₂;
Ac-D-hArg(Et)₂-D-hArg(Et)₂-Gly-Cys-Phe-D-Trp-Lys-Thr-Cys-Thr-NH₂;
Ac-Cys-Lys-Asn-4-Cl-Phe-Phe-D-Trp-Lys-Thr-Phe-Thr-Ser-D-Cys-NH₂;
Bmp-Tyr-D-Trp-Lys-Val-Cys-Thr-NH₂;
Bmp-Tyr-D-Trp-Lys-Val-Cys-Phe-NH₂;
Bmp-Tyr-D-Trp-Lys-Val-Cys-4-Cl-Phe-NH₂;
Bmp-Tyr-D-Trp-Lys-Val-Cys-β-Nal-NH₂;
H-D-β-Nal-Cys-Tyr-D-Trp-Lys-Val-Cys-Thr-NH₂;
H-D-Phe-Cys-Tyr-D-Trp-Lys-Abu-Cys-Thr-NH₂;
H-D-Phe-Cys-Tyr-D-Trp-Lys-Abu-Cys-β-Nal-NH₂;
H-pentafluoro-D-Phe-Cys-Tyr-D-Trp-Lys-Val-Cys-Thr-NH₂;
Ac-D-β-Nal-Cys-pentafluoro-Phe-D-Trp-Lys-Val-Cys-Thr-NH₂;
H-D-β-Nal-Cys-Tyr-D-Trp-Lys-Val-Cys-β-Nal-NH₂;
H-D-Phe-Cys-Tyr-D-Trp-Lys-Val-Cys-β-Nal-NH₂;
H-D-β-Nal-Cys-Tyr-D-Trp-Lys-Abu-Cys-Thr-NH₂;
H-D-4-Cl-Phe-Cys-Tyr-D-Trp-Lys-Abu-Cys-Thr-NH₂;
Ac-D-4-Cl-Phe-Cys-Tyr-D-Trp-Lys-Abu-Cys-Thr-NH₂;
H-D-Phe-Cys-β-Nal-D-Trp-Lys-Val-Cys-Thr-NH₂;
H-D-Phe-Cys-Tyr-D-Trp-Lys-Cys-Thr-NH₂;
cyclo[Pro-Phe-D-Trp-Lys(Me)-Thr-Phe];

cyclo[Pro-Phe-D-Trp-Lys(Me)-Thr-Phe];
cyclo[Pro-Phe-D-Trp-Lys-Thr-Phe(Me)];
cyclo[Ala(Me)-Tyr-D-Trp-Lys-Thr-Phe];
cyclo[Pro-Tyr-D-Trp-Lys-Thr-Phe];
cyclo[Pro-Phe-D-Trp-Lys-Thr-Phe];
cyclo[Pro-Phe-L-Trp-Lys-Thr-Phe];
cyclo[Pro-Phe-D-Trp(F)-Lys-Thr-Phe];
cyclo[Pro-Phe-Trp(F)-Lys-Thr-Phe];
cyclo[Pro-Phe-D-Trp-Lys-Ser-Phe];
cyclo[Pro-Phe-D-Trp-Lys-Thr-4-Cl-Phe];
cyclo[D-Ala-D-Phe(Me)-D-Thr-D-Lys-Trp-D-Phe];
cyclo[D-Ala-D-Phe(Me)-D-Val-Lys-D-Trp-D-Phe];
cyclo[D-Ala-D-Phe(Me)-D-Thr-Lys-D-Trp-D-Phe];
cyclo[D-Abu-D-Phe(Me)-D-Val-Lys-D-Trp-D-Tyr];
cyclo[Pro-Tyr-D-Trp-t-4-AchxAla-Thr-Phe];
cyclo[Pro-Phe-D-Trp-t-4-AchxAla-Thr-Phe];
cyclo[Ala(Me)-Tyr-D-Trp-Lys-Val-Phe];
cyclo[Ala(Me)-Tyr-D-Trp-t-4-AchxAla-Thr-Phe];
cyclo[Pro-Tyr-D-Trp-4-Amp-Thr-Phe]
cyclo[Pro-Phe-D-Trp-4-Amp-Thr-Phe]
cyclo[Ala(Me)-Tyr-D-Trp-4-Amp-Thr-Phe]
cyclo[Asn-Phe-Phe-D-Trp-Lys-Thr-Phe-Gaba];
cyclo[Asn-Phe-Phe-D-Trp-Lys-Thr-Phe-Gaba-Gaba];
cyclo[Asn-Phe-D-Trp-Lys-Thr-Phe];
cyclo[Asn-Phe-Phe-D-Trp-Lys-Thr-Phe-NH(CH$_2$)$_4$CO];
cyclo[Asn-Phe-Phe-D-Trp-Lys-Thr-Phe-β-Ala];
cyclo[Asn-Phe-Phe-D-Trp-Lys-Thr-Phe-D-Glu]-OH;
cyclo[Phe-Phe-D-Trp-Lys-Thr-Phe];
cyclo[Phe-Phe-D-Trp-Lys-Thr-Phe-Gly];
cyclo[Phe-Phe-D-Trp-Lys-Thr-Phe-Gaba];
cyclo[Asn-Phe-Phe-D-Trp-Lys-Thr-Phe-Gly];
cyclo[Asn-Phe-Phe-D-Trp(F)-Lys-Thr-Phe-Gaba];
cyclo[Asn-Phe-Phe-D-Trp(NO$_2$)-Lys-Thr-Phe-Gaba];
cyclo[Asn-Phe-Phe-Trp(Br)-Lys-Thr-Phe-Gaba];
cyclo[Asn-Phe-D-Trp-Lys-Thr-Phe(I)-Gaba];
cyclo[Asn-Phe-D-Trp-Lys-Thr-Tyr(tBu)-Gaba];
cyclo[Bmp-Lys-Asn-Phe-Phe-D-Trp-Lys-Thr-Phe-Thr-Pro-Cys]-OH;
cyclo[Bmp-Lys-Asn-Phe-Phe-D-Trp-Lys-Thr-Phe-Thr-Pro-Cys]-OH;
cyclo[Bmp-Lys-Asn-Phe-Phe-D-Trp-Lys-Thr-Phe-Thr-Tpo-Cys]-OH;
cyclo[Bmp-Lys-Asn-Phe-Phe-D-Trp-Lys-Thr-Phe-Thr-Leu(Me)-Cys]-OH;
cyclo[Phe-Phe-D-Trp-Lys-Thr-Phe-Phe-Gaba];
cyclo[Phe-Phe-D-Trp-Lys-Thr-Phe-D-Phe-Gaba];
cyclo[Phe-Phe-D-Trp(F)-Lys-Thr-Phe-Phe-Gaba];
cyclo[Asn-Phe-Phe-D-Trp-Lys(Ac)-Thr-Phe-NH—(CH$_2$)$_3$—CO];
cyclo[Lys-Phe-Phe-D-Trp-Lys-Thr-Phe-Gaba];
cyclo[Lys-Phe-Phe-D-Trp-Lys-Thr-Phe-Gaba];
cyclo[Orn-Phe-Phe-D-Trp-Lys-Thr-Phe-Gaba]; and
H-Cys-Phe-Phe-D-Trp-Lys-Thr-Phe-Cys-NH$_2$;
wherein a disulfide bond exists in the compound having two Cys residues and where the amine nitrogen of one or more amide peptide bond substituted with a methyl group.

18. A method of binding one or more of human somatostatin subtype receptors-1, -2, -3, -4 and -5, which comprises the step of administering a compound of claim 17 or a pharmaceutically acceptable salt thereof to a recipient in need thereof.

19. A method of eliciting a somatostatin agonist effect, which comprises the step of administering a compound of claim 17 or a pharmaceutically acceptable salt thereof to a recipient in need thereof.

20. A method of treating a disease or condition in a human or a mammal in need thereof, which comprises administering a compound of claim 17 or a pharmaceutically acceptable salt thereof to said human or mammal, wherein said disease or condition is selected from the group consisting of Cushings Syndrome, gonadotropinoma, hyperparathyroidism, Paget's disease, VIPoma, nesidioblastosis, hyperinsulinism, gastrinoma, Zollinger-Ellison Syndrome, hypersecretory diarrhea related to AIDS and other conditions, irritable bowel syndrome, pancreatitis, Crohn's Disease, systemic sclerosis, thyroid cancer, psoriasis, hypotension, panic attacks, sclerodoma, small bowel obstruction, gastroesophageal reflux, duodenogastric reflux, Graves' Disease, polycystic ovary disease, upper gastrointestinal bleeding, pancreatic pseudocysts, pancreatic ascites, leukemia, meningioma, cancer cachexia, acromegaly, restenosis, hepatoma, lung cancer, melanoma, inhibiting the accelerated growth of a solid tumor, decreasing body weight, treating insulin resistance, Syndrome X, prolonging the survival of pancreatic cells, fibrosis, hyperlipidemia, hyperamylinemia, hyperprolactinemia and prolactinomas.

\* \* \* \* \*